US006892093B2

(12) United States Patent
Brodnick

(10) Patent No.: US 6,892,093 B2
(45) Date of Patent: May 10, 2005

(54) METHOD AND APPARATUS FOR REAL TIME DISPLAY OF FILTERED ELECTROCARDIOGRAM DATA

(75) Inventor: Donald Eugene Brodnick, Cedarburg, WI (US)

(73) Assignee: GE Medical Systems Information Technologies Inc., Milwaukee, WI (US)

( * ) Notice: Subject to any disclaimer, the term of this patent is extended or adjusted under 35 U.S.C. 154(b) by 428 days.

(21) Appl. No.: 10/064,634

(22) Filed: Aug. 1, 2002

(65) Prior Publication Data

US 2004/0024327 A1 Feb. 5, 2004

(51) Int. Cl.$^7$ .............................................. A61B 5/04
(52) U.S. Cl. ...................... 600/523; 600/509; 345/440; 345/441
(58) Field of Search ................................. 600/523–525, 600/509; 607/2, 59; 345/440–442

(56) References Cited

U.S. PATENT DOCUMENTS

| | | | | |
|---|---|---|---|---|
| 3,793,626 | A | | 2/1974 | Zambuto ................. 340/172.5 |
| 4,812,996 | A | * | 3/1989 | Stubbs ...................... 702/123 |
| 5,357,969 | A | | 10/1994 | Herleikson ................. 128/696 |
| 5,474,079 | A | | 12/1995 | Brodnick et al. ........... 128/711 |
| 5,827,195 | A | | 10/1998 | Lander ...................... 600/509 |
| 5,891,045 | A | * | 4/1999 | Albrecht et al. ............ 600/509 |
| 5,908,393 | A | * | 6/1999 | Albrecht et al. ............ 600/509 |
| 5,953,018 | A | | 9/1999 | Lam .......................... 354/440 |
| 5,956,013 | A | | 9/1999 | Raj et al. .................... 345/134 |
| 6,047,206 | A | * | 4/2000 | Albrecht et al. ............ 600/509 |
| 6,351,664 | B1 | | 2/2002 | Brodnick ................... 600/509 |

FOREIGN PATENT DOCUMENTS

JP 070120502 5/1995 ........... G01R/13/20

OTHER PUBLICATIONS

PCT Search Report for GP 0317966.0.
J. J. Bailey, A. S. Berson, A. Garson, Jr., L. G. Horan, P.W. Macfarlane, D. W. Mortara, and C. Zywietz; "Recommendations for Standardization and Specifications in Automated Electrocardiography: Bandwidth and Digital Signal Processing—A Report for Health Professionals by an Ad Hoc Writing Group of the Committee on Electrocardiography and Cardiac Electrophysiology of the Council on Clinical Cardiology, American Heart Association," AHA Scientific Council—Recommendations in ERlectrocardiography Special Report Circulation vol. 81, No. 2, Feb. 1990; pp. 730–739.

* cited by examiner

Primary Examiner—Carl Layno
(74) Attorney, Agent, or Firm—Cantor Colburn LLP

(57) ABSTRACT

A method for displaying waveform data on a display device is disclosed. In an exemplary embodiment, the method includes apportioning a display region into a first portion and a second portion immediately adjacent to the first portion. The first portion is used to display a first segment of the waveform data including the most recently received data extending back to a determined delay period. The second portion is used to display a second segment of the waveform data, the second segment including the remainder of the waveform data. The data displayed in the first portion has a continuously varying amplitude level adjustment applied thereto for partial baseline correction thereof, while the data displayed in the second portion has a corrected baseline amplitude adjustment with no further amplitude level adjustment applied thereto.

25 Claims, 18 Drawing Sheets

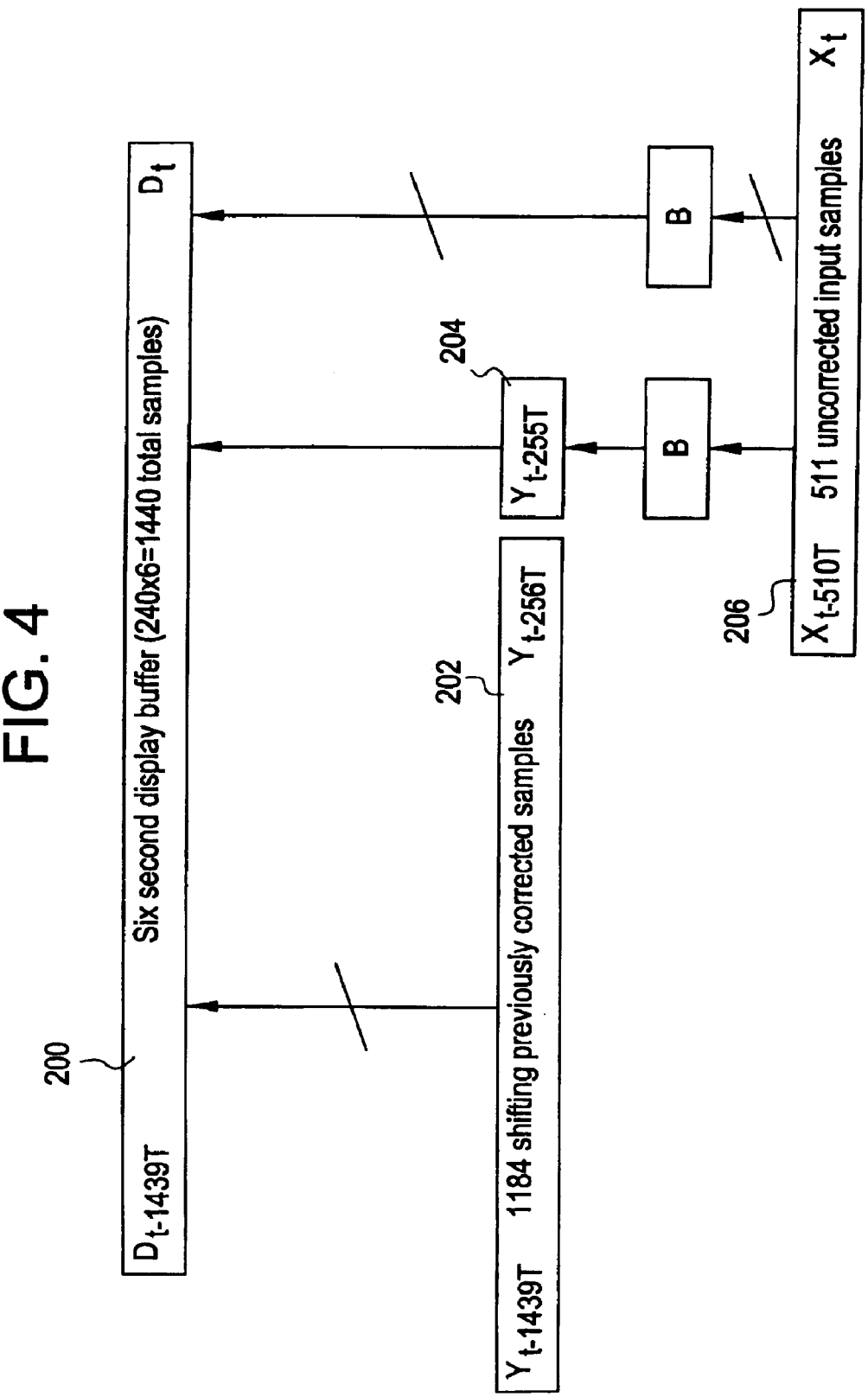

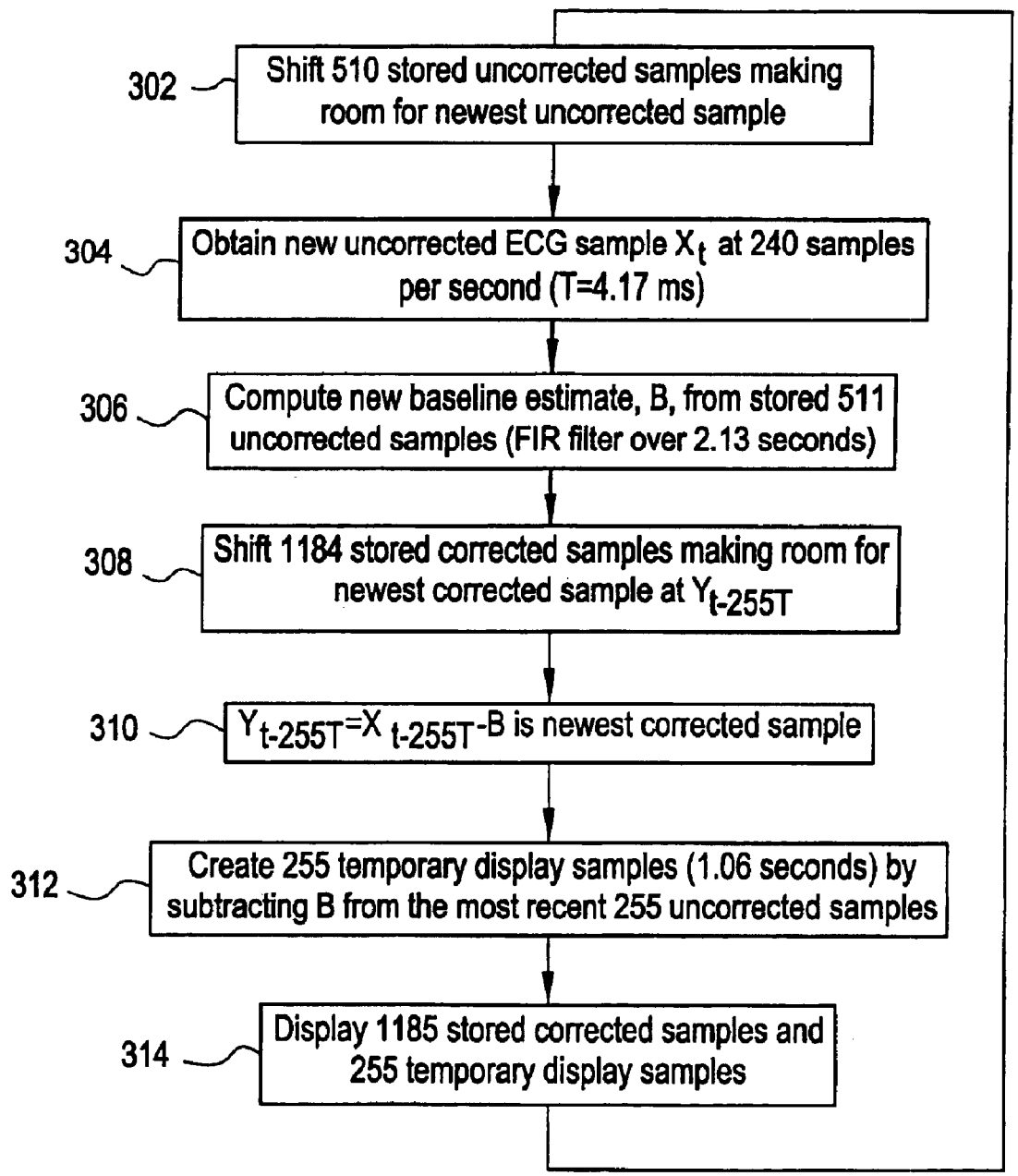

METHOD AND APPARATUS FOR REAL TIME DISPLAY OF FILTERED ELECTROCARDIOGRAM DATA

BACKGROUND OF INVENTION

The present disclosure relates generally to methods of real time display of filtered waveform data and, more particularly, to a method and apparatus for real time display of filtered electrocardiogram data.

An electrocardiogram (ECG) of a cardiac cycle is detected across sense electrode pairs located on the surface of a patient's body, and is a repetitive waveform characterized by a periodic PQRST electrical activation sequence of the upper and lower heart chambers. The PQRST sequence is associated with the sequential depolarization and contraction of the atria followed by the depolarization and contraction of the ventricles, and successive PQRST complexes are separated by a baseline or isoelectric region.

As shown in FIG. 1, The PQRST electrical activation sequence commences with the P-wave, which is indicative of the depolarization and contraction of the atria. Following is the QRS complex, which is indicative of the depolarization and contraction of the ventricles. The T-wave at the termination of the ST segment time delay is associated with re-polarization of the ventricles. The PQRST electrical activation sequence with intact A-V activation detected across a sense electrode pair is fairly predictable in shape. The P-wave, R-wave and T-wave events occurring in sequence in the range of normal heart rates are usually readily recognized by visual examination of the external ECG recorded by applied body surface electrodes that are correctly oriented with the depolarization waves. The P-wave and the R-wave are readily sensed by sense amplifiers of a monitor or therapy delivery device coupled with appropriately placed sense electrode pairs.

The ST segment of the ECG is typically close in amplitude to the baseline or isoelectric amplitude of the signal sensed between PQRST sequences, depending on the sense electrode pair location. During episodes of myocardial ischemia, the ST segment amplitude is elevated or depressed (depending on positioning of the ECG sense electrodes in relation to the heart) from baseline. These ST segment deviations can be readily recognized by visual examination.

However, the ECG signals are typically subject to low frequency noise (such as, for example, from respiration that occurs at a lower rate than the heart rate), thus resulting in baseline drift. Such an effect can render the ECG waveform difficult to read, especially in a display device having multiple ECG waveforms presented simultaneously. Presently, there are filtering techniques in existence that aggressively remove the baseline drift, but which also result in a distorted portion of ECG waveform (e.g., the ST segment) and/or introduce a delay in the display presentation. If a filtering technique is aimed at minimizing the distortion or eliminating a delay, this typically comes at the price of not aggressively correcting the baseline. Accordingly, it is desirable to be able to compensate for baseline drift and low frequency noise, while maintaining the integrity of the ECG waves and complexes without introducing a delay in the display thereof.

SUMMARY OF INVENTION

The above discussed and other drawbacks and deficiencies of the prior art are overcome or alleviated by a method for displaying waveform data on a display device. In an exemplary embodiment, the method includes apportioning a display region into a first portion and a second portion immediately adjacent to the first portion. The first portion is used to display a first segment of the waveform data including the most recently received data extending back to a determined delay period. The second portion is used to display a second segment of the waveform data, the second segment including the remainder of the waveform data. The data displayed in the first portion has a continuously varying amplitude level adjustment applied thereto for partial baseline correction thereof, while the data displayed in the second portion has a corrected baseline amplitude adjustment with no further amplitude level adjustment applied thereto.

In another aspect, a method of filtering and displaying sequential waveform data samples includes shifting a sequence of stored uncorrected data samples, and then receiving and storing a new uncorrected data sample. A baseline estimate correction is computed using the stored uncorrected data samples and the new uncorrected data sample. Then, a sequence of stored corrected data samples is shifted and a new corrected data sample is determined by applying the baseline estimate correction to a specific one of the stored uncorrected data samples. A sequence of temporary display data samples is created by applying the baseline correction to each of the stored uncorrected data samples that were stored subsequent to the specific stored uncorrected data sample, as well as to the new uncorrected data sample. Then, the sequence of corrected data samples, the new corrected data sample, and the sequence of temporary display data samples are each displayed.

In still a further aspect, an electrocardiogram (ECG) system includes a set of electrodes for detecting ECG signals from a subject and signal condition circuitry for conditioning the ECG signals detected by the set of electrodes. A processor is used for processing conditioned signals from the signal condition circuitry. In addition, a display for displaying ECG waveform data produced by the processor further includes a display region having a first portion and a second portion immediately adjacent to the first portion. The first portion is used to display a first segment of the waveform data representing the most recently received data extending back to a determined delay period, while the second portion is used to display a second segment of the waveform data representing the remainder of the waveform data. The waveform data displayed in the first portion has a continuously varying amplitude level adjustment applied thereto for partial baseline correction thereof, and the data displayed in the second portion has a corrected baseline amplitude adjustment with no further amplitude level adjustment applied thereto.

BRIEF DESCRIPTION OF DRAWINGS

Referring to the exemplary drawings wherein like elements are numbered alike in the several Figures:

FIG. 4 is a schematic diagram illustrating an exemplary data filtering and display technique, in accordance with an embodiment of the invention;

FIG. 5 is a flow diagram further illustrating the data filtering and display technique shown in FIG. 4;

DETAILED DESCRIPTION

Disclosed herein is a method and apparatus for real time display of filtered electrocardiogram data. Briefly stated, a delayed symmetrical finite impulse response filter (FIR) is implemented to produce a continuously adjusted DC level portion of a display region. A continuous scrolling display is thereby provided in which a first portion of the display features a more recent portion of the overall waveform data having a continuously level adjusted, partially corrected baseline. In addition, a second portion of the display features an earlier portion of the overall waveform data having a substantially corrected baseline that scrolls at constant amplitude. As a result of this technique, the ST segment of a displayed ECG waveform remains undistorted.

In one embodiment, the symmetrical FIR is designed to be, in effect, a triangular impulse response with a total width of a little more than 2 seconds. Accordingly, a delay of about 1 second is implemented before filtering and thus the continuously adjusted DC level portion (i.e., the first portion) of the display region is at the right side of the display, covering a display distance of approximately one second. However, the delay may be implemented over a larger time range from about 0.5 seconds to about 3.0 seconds. Conventionally, for ECG systems, new data enters onto the display area at the right edge thereof while older data scrolls across the area in a leftward direction. In order to implement the baseline correction, the first portion of the display area is completely repainted every screen refresh time while, in contrast, the data shown in the second portion of the display area is simply scrolled (i.e., shifted to the left) by a constant count of pixels every refresh time. Such a display is possible with modern computer video displays capable of repainting the entire screen every vertical refresh period (approximately 70 times per second).

Figure 1:
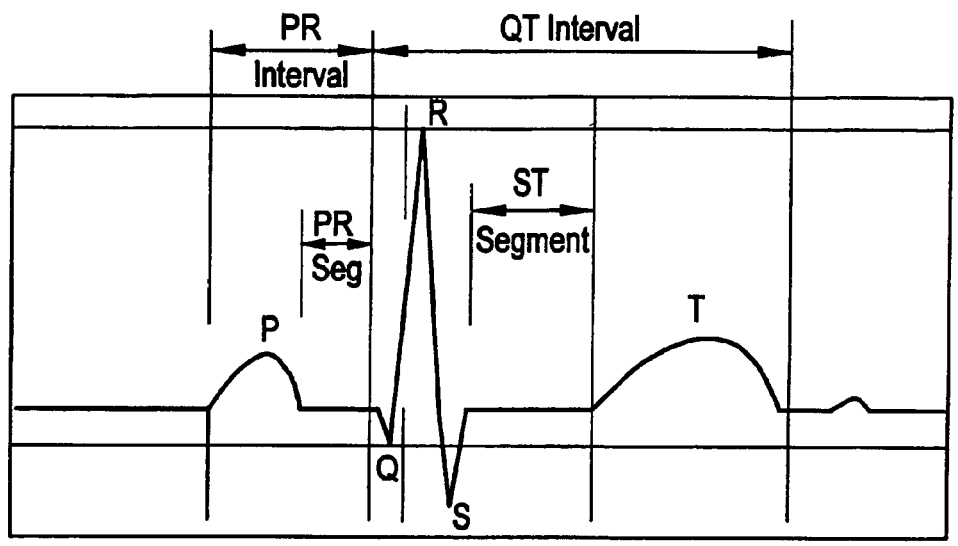
FIG. 1 is a schematic representation of an ECG waveform.
Figure 2:
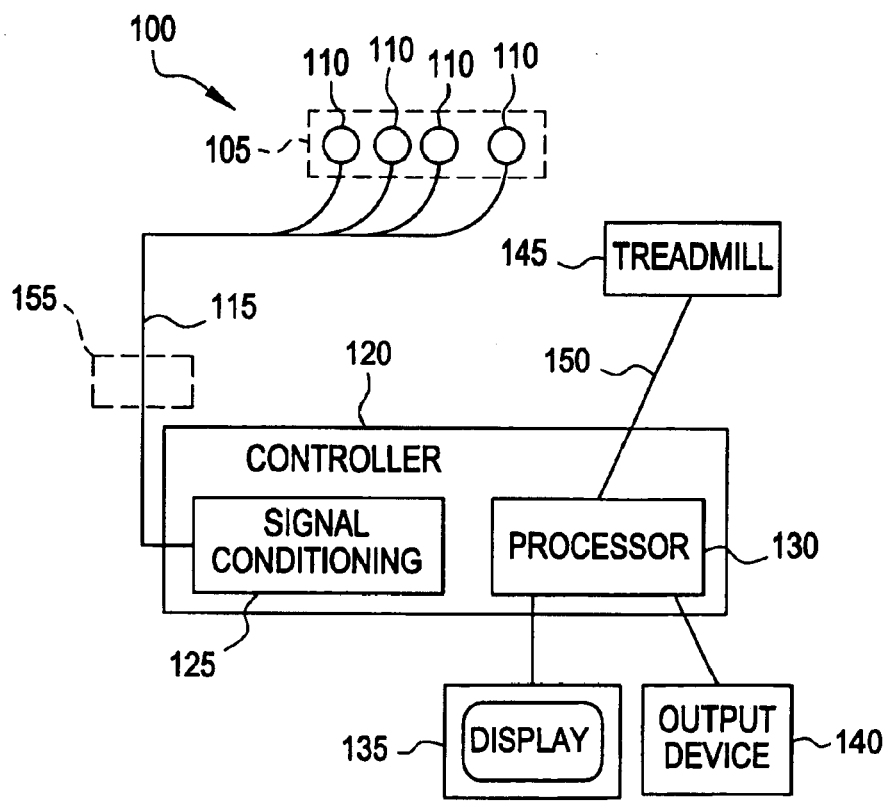
FIG. 2 is a schematic block diagram of an exemplary ECG system suitable for practicing an embodiment of the present disclosure.

Referring initially to FIG. 2, there is shown an exemplary ECG system 100 suitable for practicing an embodiment of the present disclosure. The system 100 may, for example, be used in a clinical setting or perhaps during the physiologic stress testing of a patient's heart. In an exemplary embodiment, the system 100 includes a set 105 of electrodes 110, which may be standard ECG electrodes, or possibly an array of electrodes applied to cover the anterior, lateral and posterior areas of the patient's torso. While the electrodes 110 function separately from one another, they may be physically affixed together to form a flexible band or other arrangement.

In addition, the system 100 further includes a set of leads 115 that connect the electrodes to a system controller 120. The controller 120 includes signal conditioning circuitry 125 and a processor 130. The signal conditioning circuitry 125 receives analog signals from the leads 115 as inputs thereto, and provides as outputs conditioned digital signals to the processor 130. In turn, the processor 130 processes the conditioned signals to produce output results thereafter provided to a connected display 135 and/or to an output device 140, such as a printer. If used in a stress testing application, the processor 130 may further control an exercise device, such as a treadmill 145 having a programmable slope and walking speed, through control signals supplied through a cable 150. Similarly, an optional recording device 155 of an ambulatory system may be used to record signals from the leads for an extended period of time (e.g., 24 hours). The recording device 155 then is connected to the controller 120 to permit the controller 120 to process the recorded data.

Figure 3A:
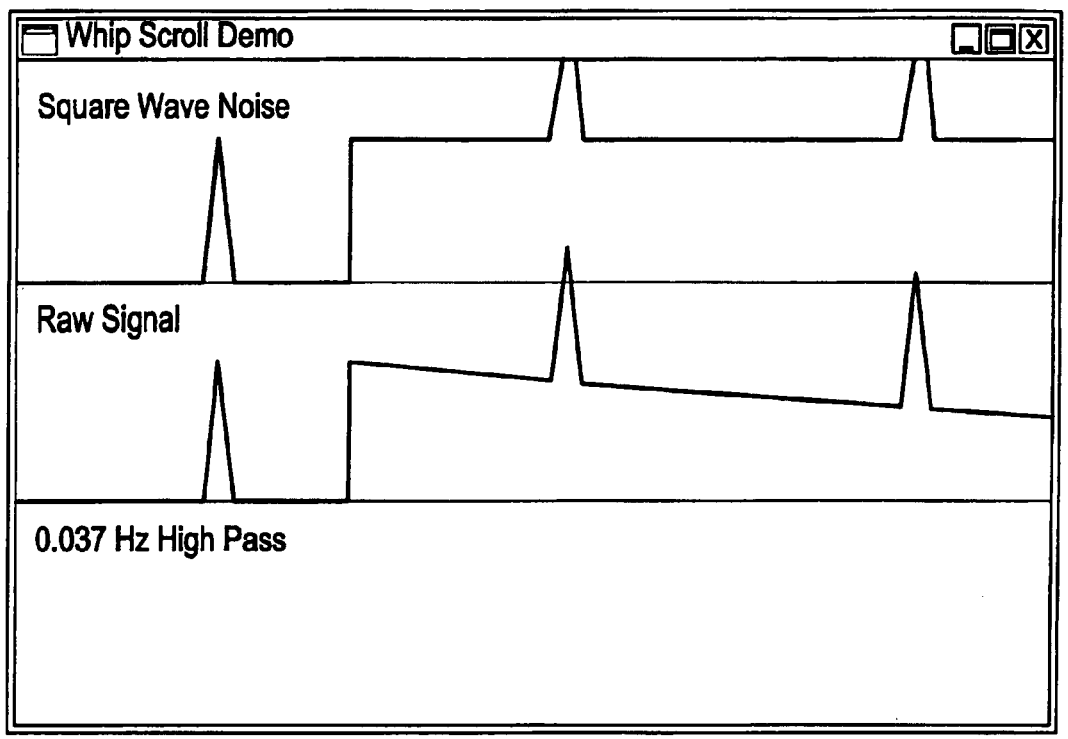
FIGS. 3($a$) through 3($f$) are waveform displays illustrating conventional data filtering techniques as applied to a square wave noise disturbance.
Figure 3B:
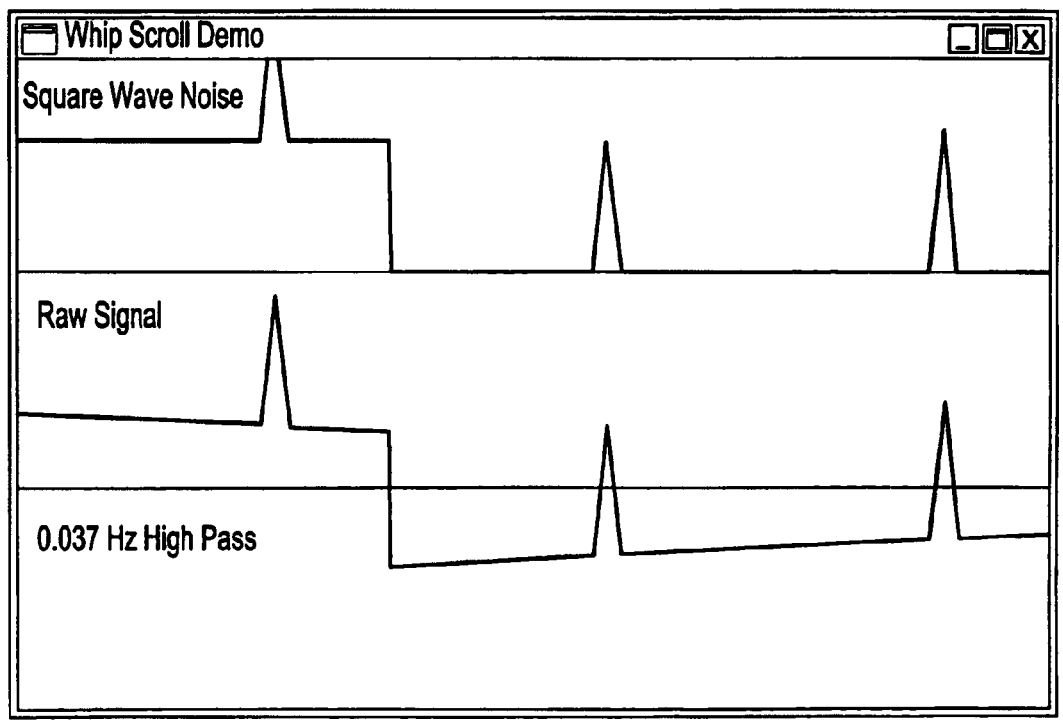

As stated previously, there are existing problems associated with the real time display of conventionally filtered ECG data, which are particularly illustrated by way of a fairly simplified example. Referring now to FIGS. 3(a) and 3(b), there is shown a pair of waveform displays of a periodic triangular impulse that mimics the general shape of the QRS complex. The upper waveform, as indicated in the figures, represents the raw signal disturbed by square wave noise, while the lower waveform represents the same signal (also disturbed by square wave noise) as filtered by a 0.037 Hz high pass filter. As can be seen, while the 0.037 Hz filter preserves the integrity of the triangular pulse, it is slow to respond with respect to returning the waveform back to its baseline level. When the square wave noise is removed, as shown in FIG. 3(b), the waveform drops below the baseline and is slow in returning upward back to the baseline.

Figure 3C:
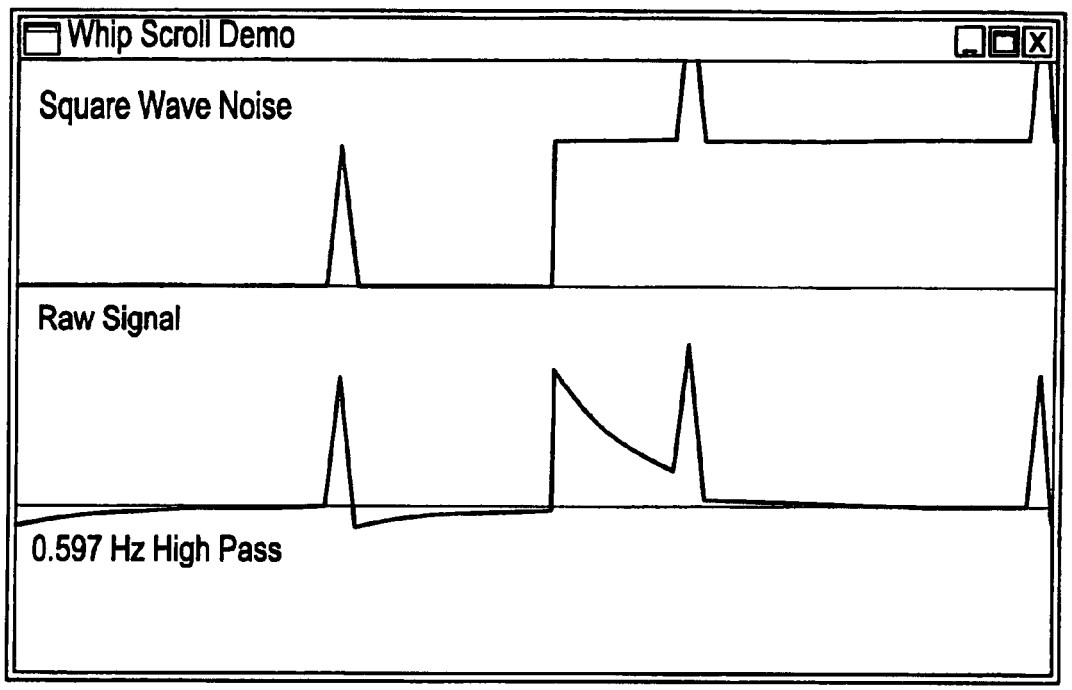
Figure 3D:
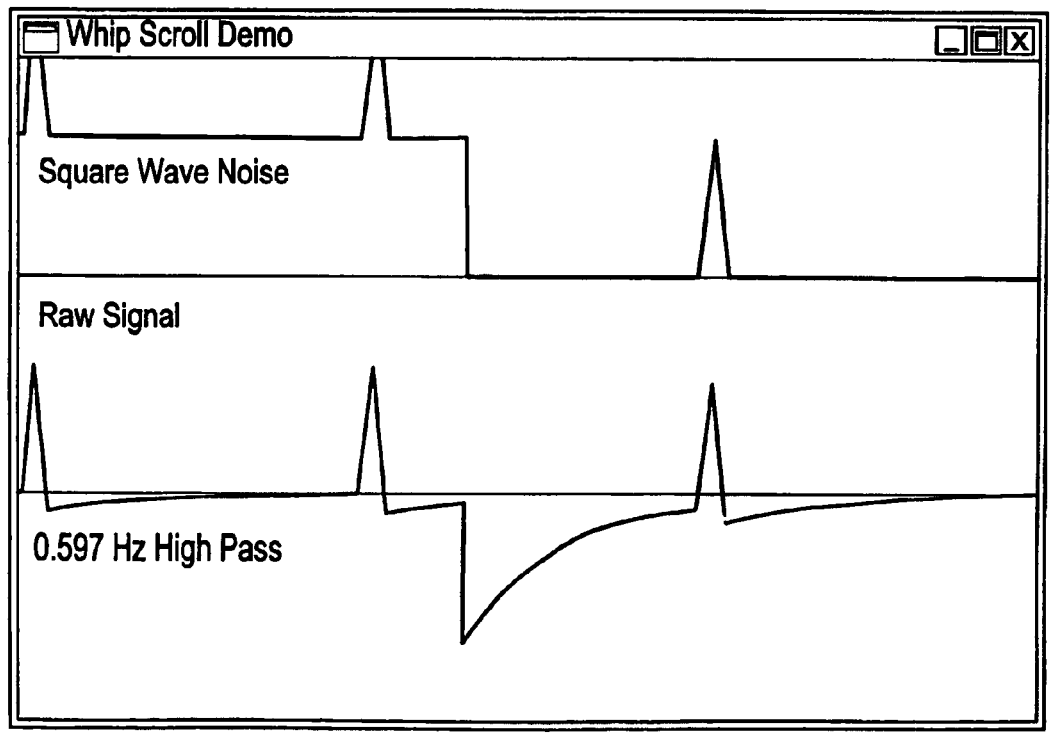
Figure 3E:
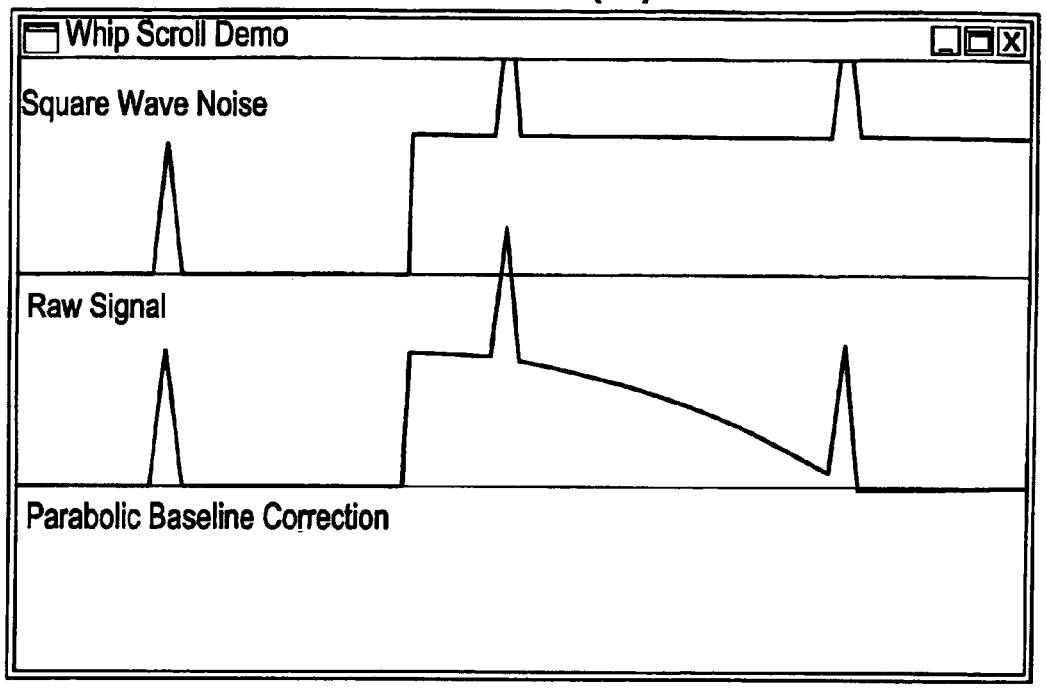
Figure 3F:
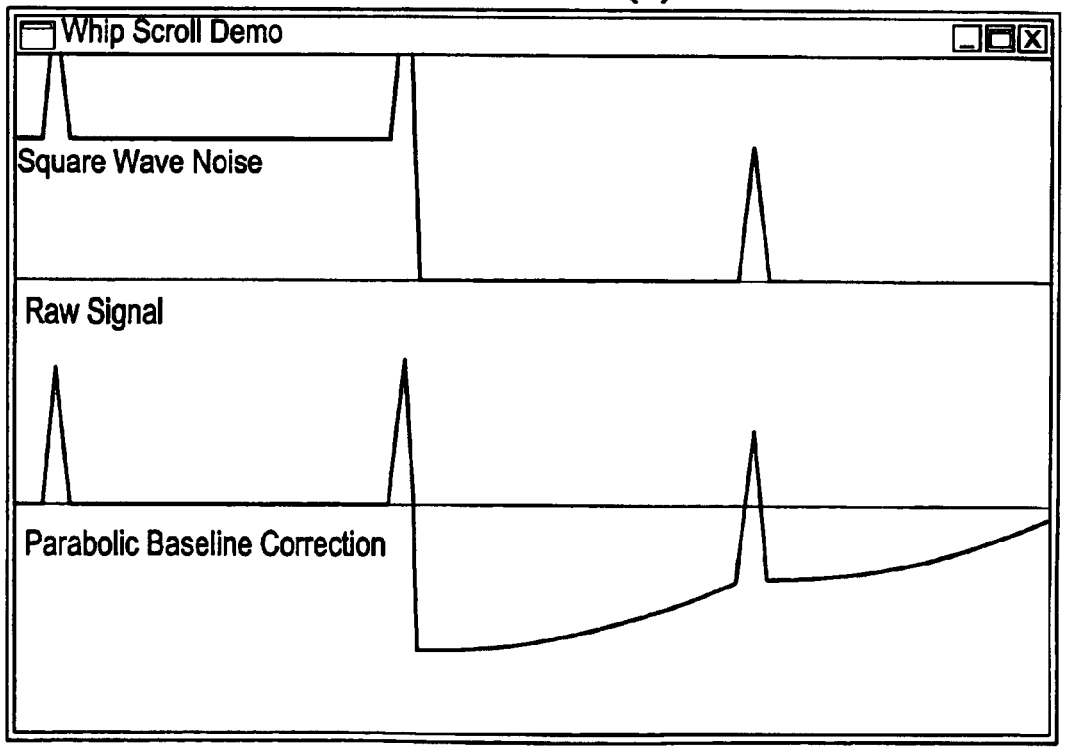

In contrast, when a 0.597 Hz high pass filter is used, there is a much quicker return to the baseline, as shown in FIGS. 3(c) and 3(d). However, it will also be noted that this filter distorts the falling edge of the triangular impulse by dipping it below the level of the beginning of the rising edge. Unfortunately, such a distortion could result in an inaccurate interpretation of an actual ECG reading. Thus, this particular type of aggressive filtering of the waveform is equally as undesirable as a slow response time. Still another type of filtering technique is what is referred to as parabolic baseline correction, and is illustrated in FIGS. 3(e) and 3(f). As can be seen, the parabolic baseline correction does not result in as much distortion as the 0.597 Hz high pass filter, but it is also not as aggressive in returning the waveform to the baseline.

Therefore, in accordance with an embodiment of the invention, there is disclosed a method and apparatus for real time display of filtered data, such as electrocardiogram data. Referring now to FIG. 4, there is shown schematic diagram illustrating the principles of the present filtering and display technique. A display buffer 200 contains the most recent ECG waveform data to be displayed, such as on the display 135 of FIG. 2. By way of example only, the ECG data is configured for a six second display buffer at a rate of 240 samples per second, with a total of 1440 data samples being displayed at any instant in time. Obviously, if a greater or lesser duration of waveform signal is displayed, or if a different sampling rate is used, then the total number of data samples displayed at once will be different.

As shown in FIG. 4, the 1440 total data samples are designated $D_t$ through $D_{t-1439T}$. The newest displayed data sample is $D_t$ (at the far right of the display buffer 200) while the oldest displayed data sample is $D_{t-1439T}$ (at the far left of the display buffer), wherein T represents a sample period of approximately 4.17 milliseconds, and t represents the current time. In this exemplary embodiment, it will be assumed that the display is refreshed at the same rate that new input samples become available.

In addition to the display buffer 200, a filtered data buffer 202 is used to store and shift baseline corrected data. The baseline corrected data in the filtered data buffer 202 is directly passed into corresponding locations in the display buffer 200. It is this baseline corrected data that is used for the display and scrolling in a second portion of the display 135. The data samples in the filtered data buffer 202 are designated $Y_{t-256T}$ through $Y_{t-1439T}$, signifying that the earliest of the baseline corrected data is displayed after about a 1.06 second delay. Immediately to the right of the filtered data buffer 202 is a storage element 204 that holds sample data designated $Y_{t-255T}$. It is here that the weighted average baseline adjustment is made to the raw sampled data before it reaches the filtered data buffer 202. Finally, an unfiltered data buffer 206 is used to store (and subsequently) shift the most recent 511 unfiltered data samples used by the FIR filter. Accordingly, the data samples contained in the unfiltered data buffer 206 are designated $X_t$ through $X_{t-510T}$, wherein $X_t$ represents the newest uncorrected input sample and $X_{t-510T}$ represents the oldest uncorrected input sample.

The symmetrical FIR filter uses all 511 of the unfiltered samples, centered on sample $X_{t-255T}$, to compute an average baseline estimate for every screen refresh.

Then, the computed baseline estimate, B, is subtracted from data sample $X_{t-255T}$ to produce $Y_{t-255T}$ which, as stated earlier, is passed directly to the display buffer as $D_{t-255T}$. Furthermore, the computed baseline estimate B is also used in displaying the most recent 255 samples ($D_t$ through $D_{t-254T}$). This is the data contained in the continuously adjusted DC level portion (i.e., the first portion) of the display region at the right side of the display 135, covering a display distance of about one second.

Referring now to FIG. 5, there is shown a flow diagram 300 illustrating the process by which the method operates to receive new ECG waveform data and display the new data, along with the most recent data samples. Beginning at block 302, each of the previously stored 511 unfiltered data samples in the unfiltered data buffer 206 is shifted over (with the previously oldest sample at $X_{t-510T}$ being eliminated). This clears the way for a new, uncorrected ECG data sample to be received in the unfiltered data buffer 206 at $X_t$, as shown at block 304.

Once the newest ECG sample is received at $X_t$, a new baseline estimate from the current 511 unfiltered samples is computed, as shown at block 306. This may be represented by the convolution expression: B=FIR$_{lowpass}$*$X_{t-nT}$ (for n=0 to 510). Then, at block 308, the previous data samples (1184 total) in the filtered data buffer 202 are shifted over to make room for the data sample shifted out of the storage element 204 that holds the sample data designated $Y_{t-255T}$. In turn, the storage element 204 is now clear to accept the latest corrected sample based on the newly computed baseline estimate B, wherein as stated earlier: $Y_{t-255T}$=$X_{t-255T}$-B. This step is shown at block 310. As also stated previously, the method proceeds to block 312, where additional "temporary" display samples are created from the most recent 255 unfiltered data samples (i.e., $X_t$ through $X_{t-254T}$) by subtracting B therefrom. Finally, at block 314, the entire display area is refreshed using the updated 1185 corrected samples and the 255 temporary display samples loaded into the display buffer 200. The source of the data sample $D_{t-nT}$ loaded into the display buffer 200 is described by:

$$D_{t-nT} = X_{t-nT} - B \text{ (for } n = 0 \text{ to } 254)$$
$$D_{t-nT} = Y_{t-nT} \text{ (for } n = 255 \text{ to } 1439)$$

Figure 6A:
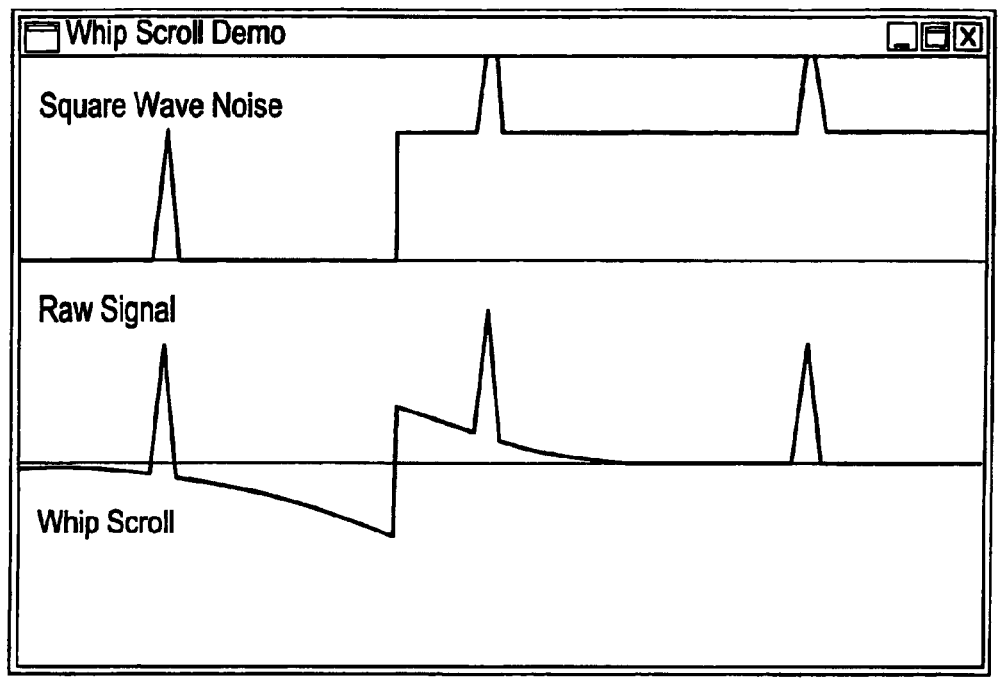
FIGS. 6(a) and 6(b) are waveform displays illustrating the results of the application of the inventive data filtering and display technique to the square wave noise disturbance.
Figure 6B:
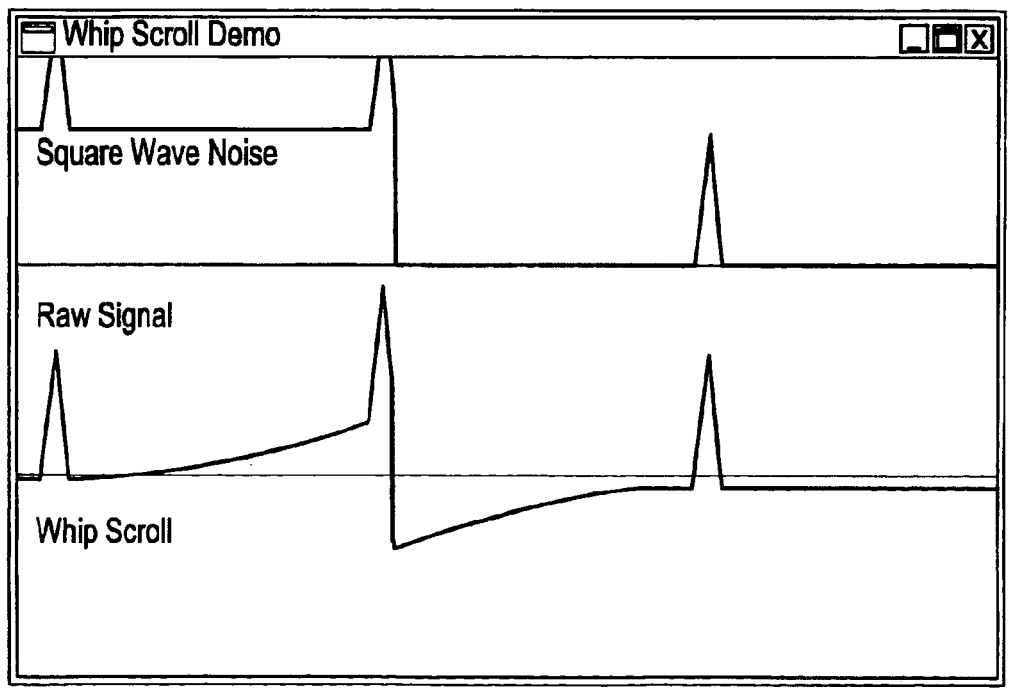

The effects of the above described method are best appreciated through observation of a moving, dynamic view of a waveform as it is scrolled across a display. Nonetheless, FIGS. 6(a) and 6(b) are somewhat illustrative of the performance of the data display method as applied to the triangular impulse/square wave disturbance examples used in FIGS. 3(a)–3(f). As will be noted, the baseline correction actually begins before the rising edge of the square wave in the raw signal, and thus the initial baseline shift upward is only roughly half that of the unfiltered waveform. This is the result of the delayed baseline correction through the symmetrical FIR filter that uses the unfiltered data samples occurring before and after the correction point of the display. It will also be noted that the time taken in returning to the baseline is favorable as compared to the aggressive 0.597 Hz filter (FIGS. 3(c) and 3(d)), only without the signal distortion.

Figure 7A:
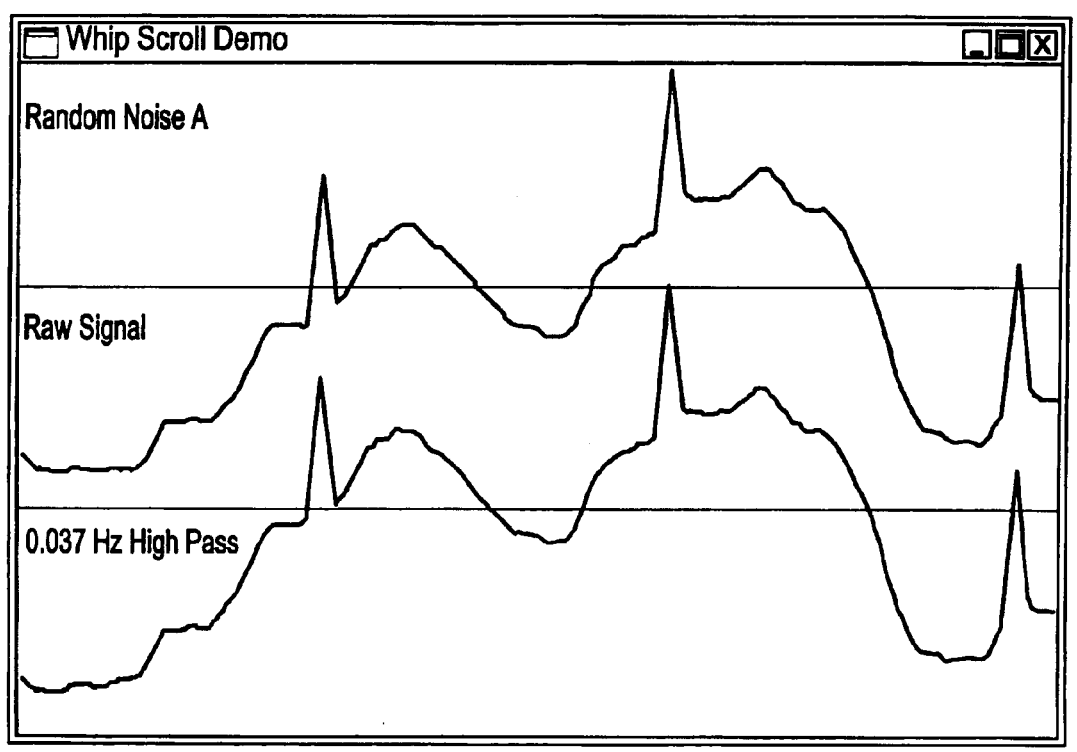
FIGS. 7(a) through 7(c) are waveform displays illustrating conventional data filtering techniques as applied to random, low frequency noise disturbance.
Figure 7B:
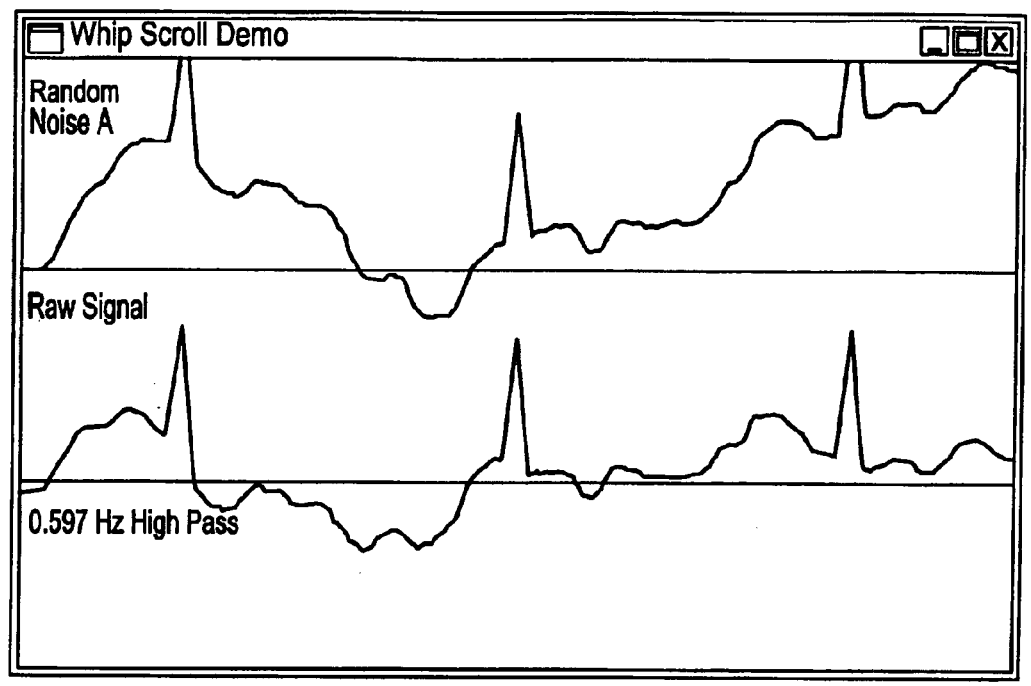
Figure 7C:
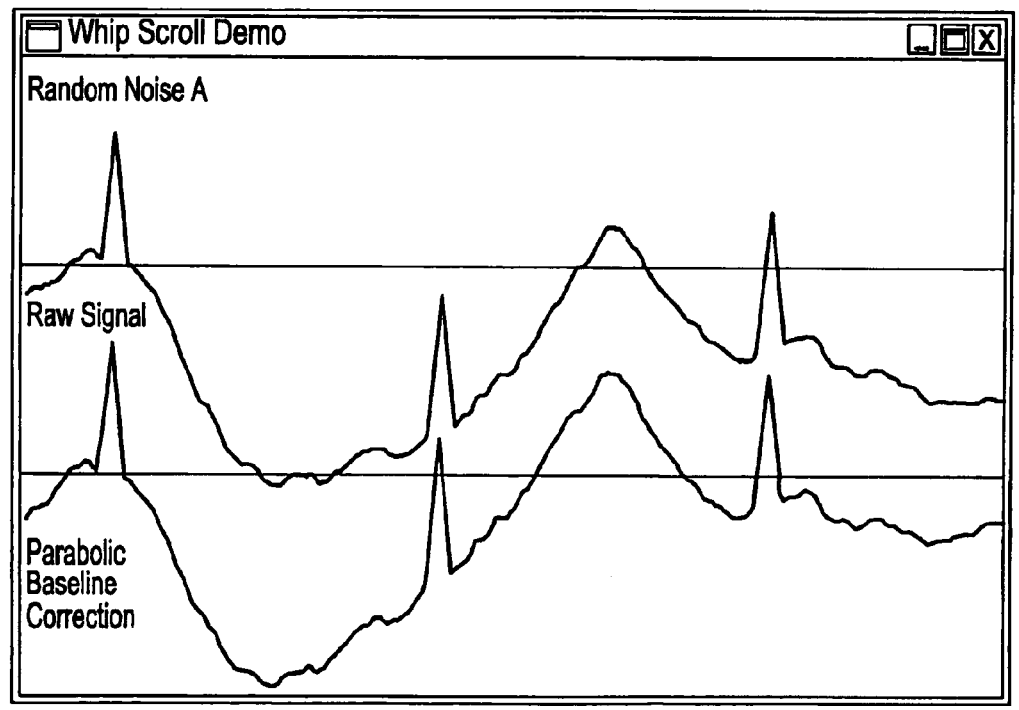

A more realistic example of random, low frequency noise imposed on the triangular impulse waveform is shown in FIGS. 7(a)–7(c). FIG. 7(a) illustrates the performance of the 0.037 Hz filter versus the unfiltered raw signal. As is shown, the 0.037 Hz filter provides very little improvement in baseline correction, with the impulses from the filtered signal being only marginally closer to the baseline than the unfiltered raw signal. In FIG. 7(b), the 0.597 Hz filter provides a much better baseline correction of the random noise, but again there is more distortion of the triangular QSR impulse itself. Once again, the parabolic baseline correction technique shown in FIG. 7(c) provides a tradeoff between baseline correction and signal distortion, but is still not as aggressive as is desirable.

In contrast, the performance of the present method on the random noise is illustrated in FIGS. 8(a) through 8(h), which are sequential images taken from a computer display screen as the waveforms are scrolled over time. In this demonstration program, the computer display screen is divided into a first portion 404 and a second portion 402, separated by the dashed line 406. It should be noted that the actual time division shown between the first and second portions of the computer display screen, being exemplary in nature, does not necessarily correspond to the specific 1440 sample display described earlier. Rather, the significance of FIGS. 8(a) through 8(h) lies in the different display techniques between the first and second portions.

Figure 8A:
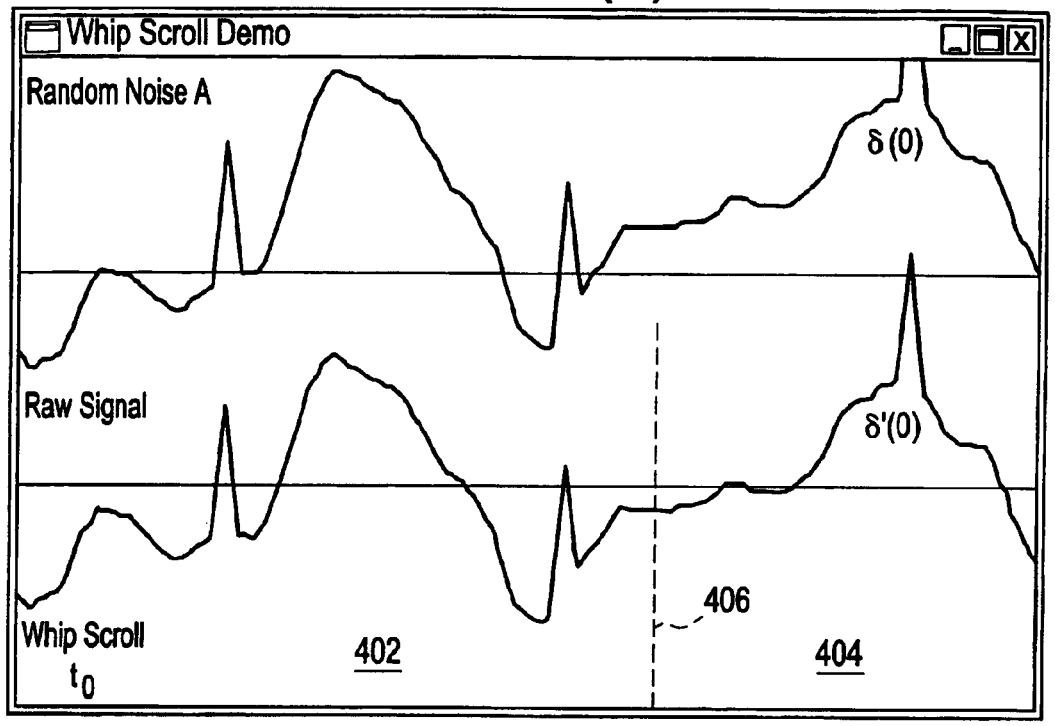
FIGS. 8(a) through 8(h) are waveform displays illustrating the results of the application of the inventive data filtering and display technique to random, low frequency noise disturbance.

FIG. 8(a) is the first image taken at an initial time $t_0$, wherein a first, raw signal triangular impulse δ(0) appears at the right side of the display. The corresponding filtered impulse, labeled δ'(0), is shown on the first portion 404 of the display screen. The second portion 402 of the display screen will scroll the waveform data in a conventional manner, while the first portion 404 provides the continuous DC level correction.

Figure 8B:
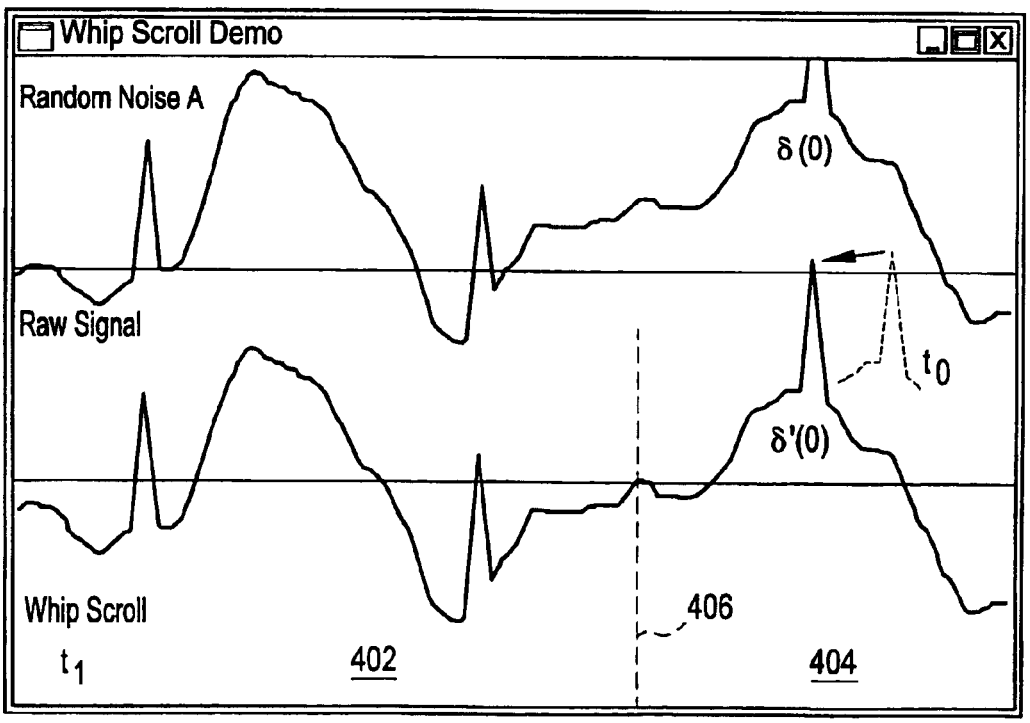
Figure 8C:
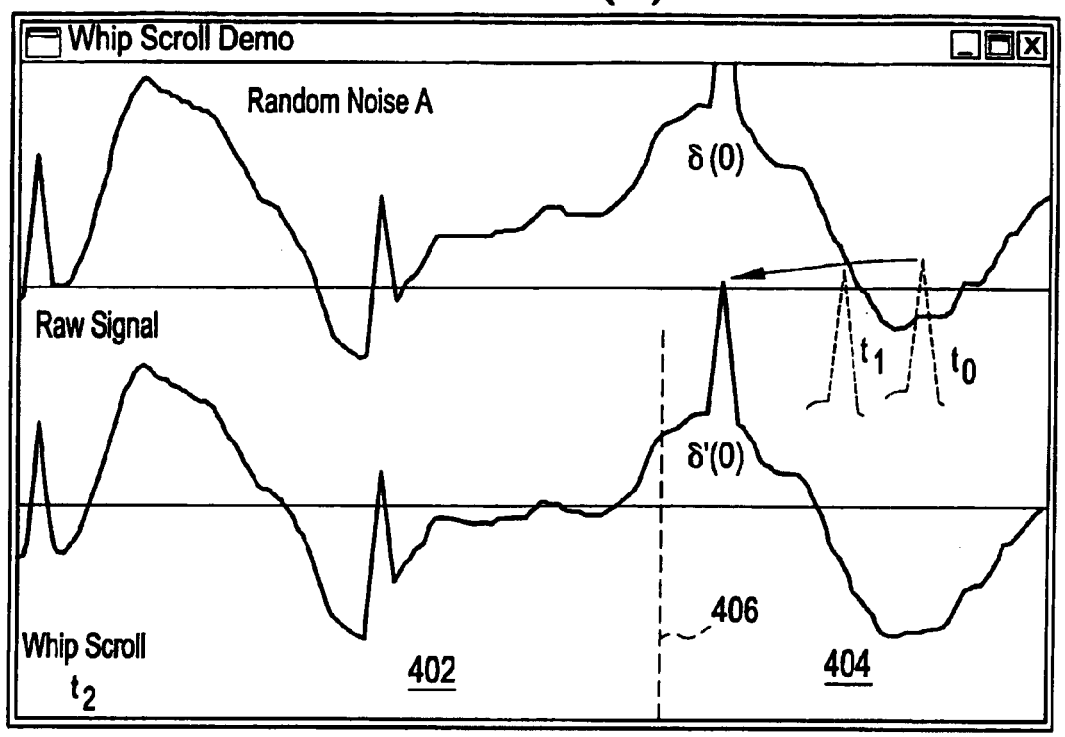

FIG. 8(b) is the screen shot taken at time $t_1$. As is shown, the position of δ'(0) with respect to the baseline has changed from its position at time $t_0$ (shown in phantom) by moving downwardly. This reflects the active baseline correction taking place within the first portion 404 of the display. More particularly, the specific baseline correction is determined by the symmetric FIR filtering, centered at dashed line 406. However, in the second portion 402 of the display, there has been no amplitude change in the filtered signal with respect to time as it is simply scrolling across. The next sequential shot is shown in FIG. 8(c), taken at time $t_2$. (It should be noted at this point that the specific time intervals between the figures are not necessarily taken at equally spaced time intervals, as the present examples are only meant to be illustrative in nature.) Once again, the position of δ'(0) has continued to decrease slightly with respect to the baseline as compared to its position at $t_1$ and $t_0$. Were the display to be viewed in real time between $t_0$ and $t_2$, the impulse δ'(0) would appear to be descending as it moves from right to left. At the same time, there would be no amplitude change in that part of the filtered waveform located in the second portion 402 as it moves from right to left.

Figure 8D:
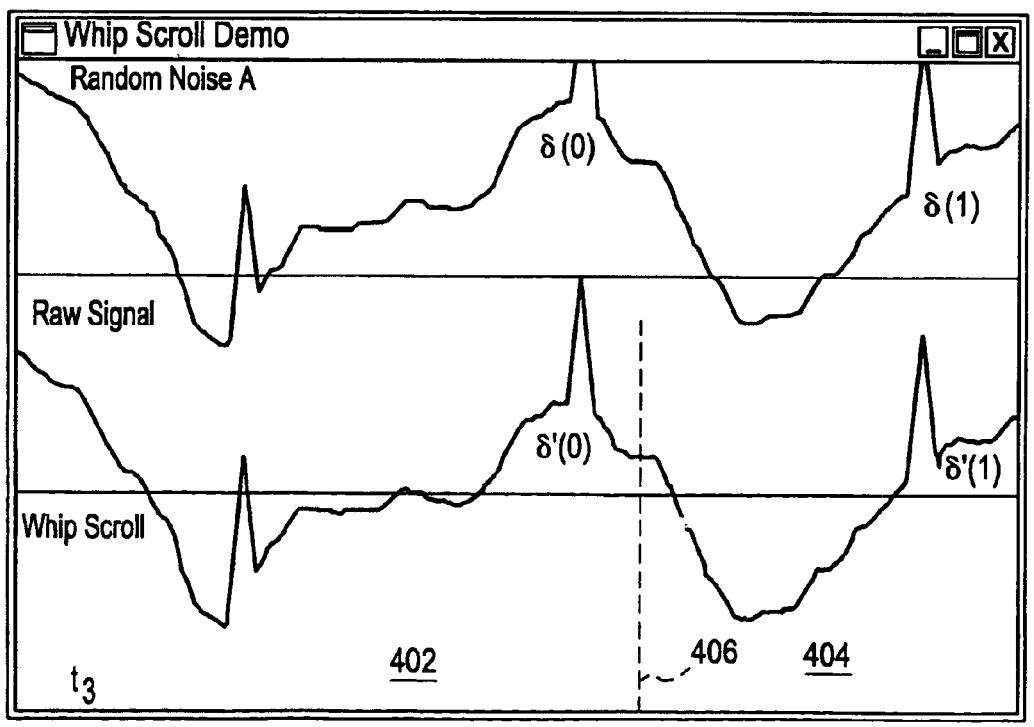
Figure 8E:
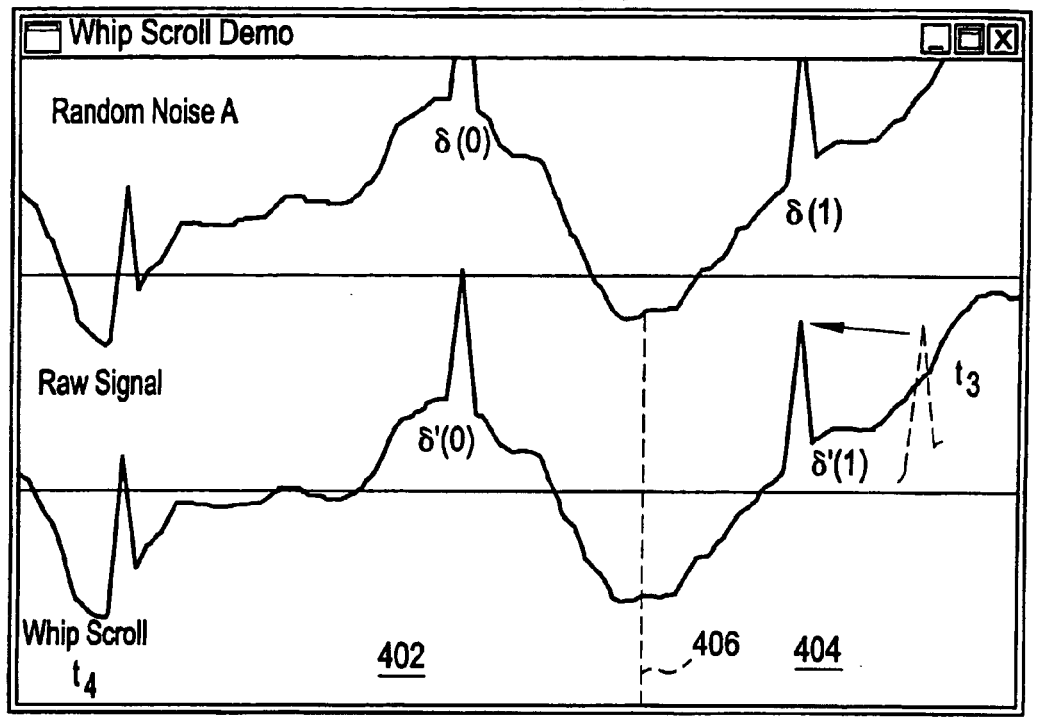

Referring now to FIG. 8(d), a new impulse δ(1) has appeared in the raw signal waveform at time $t_3$, along with the corresponding filtered impulse δ'(1) in the first portion 404 of the display. By this time, δ'(0) has scrolled over to the second portion 402, and will no longer be subjected to an amplitude correction for the remainder of its scroll time across the display. Meanwhile, in FIG. 8(e) taken at time $t_4$, the impulse δ'(1) has ascended with respect to the baseline between $t_3$ and $t_4$. During this time, it will be noted that δ'(0) has not changed its amplitude position now that it resides in the second portion 402 of the display.

Figure 8F:
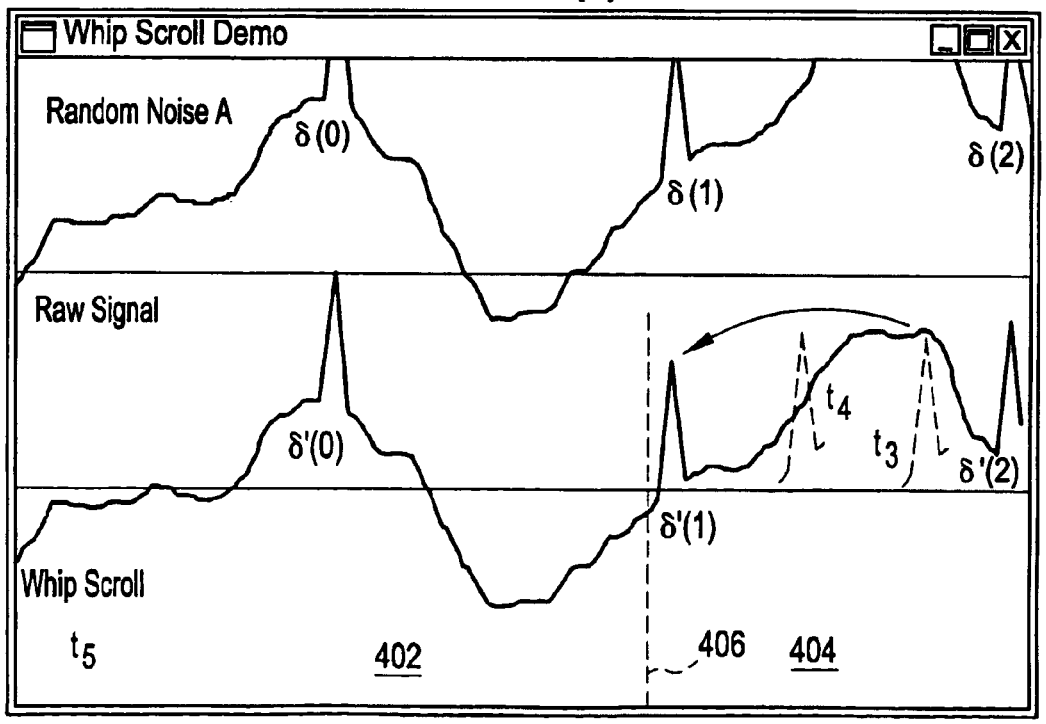
Figure 8G:
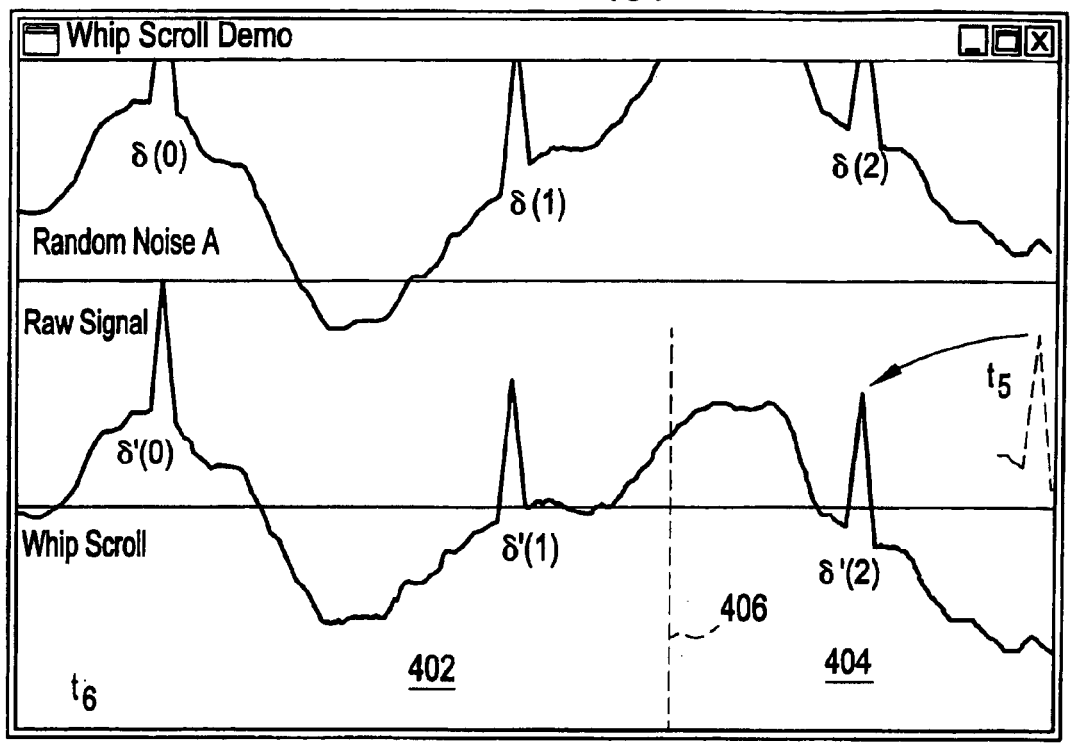
Figure 8H:
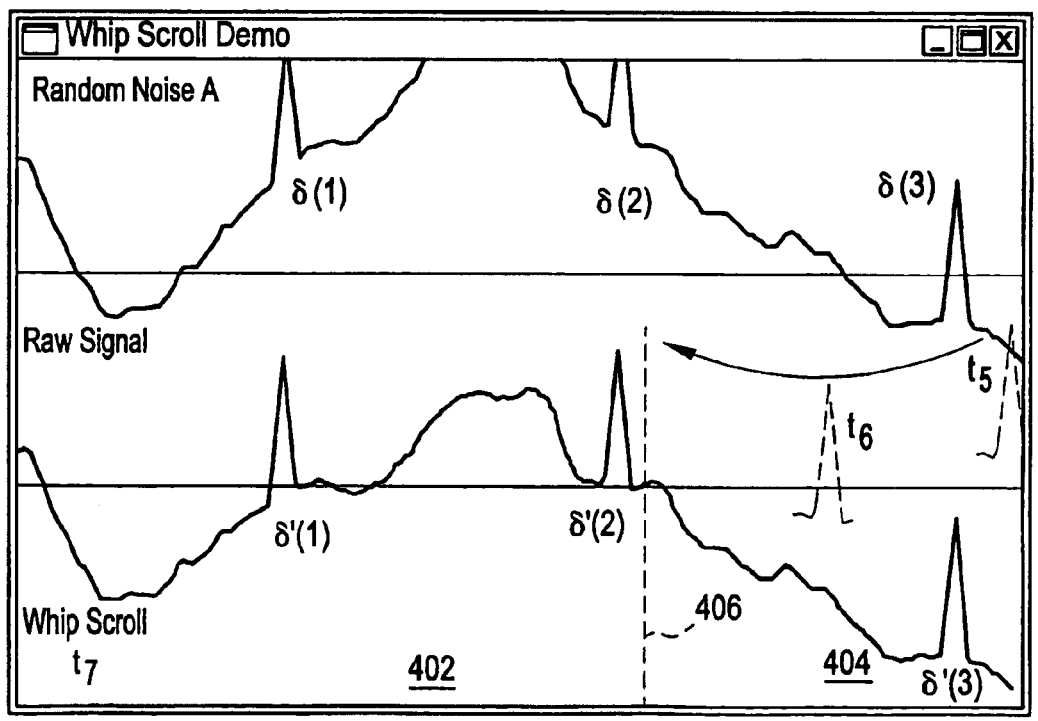

Moving forward to FIG. 8(f) at time $t_5$, it can be seen that δ'(1) has now dynamically descended from its position at $t_4$ as it is about to cross from the first portion 404 over to the second portion 402. In addition, a new impulse δ(2) (and δ'(2)) has appeared at the rightmost portion of the display. It is further noted that the amplitude position of δ'(0) has remained the same as it moves still further to the left. Then, in FIG. 8(g), taken at $t_6$, there is illustrated the downward baseline correction movement of δ'(2) while it remains in the first portion 404. Again, both δ'(1) and δ'(0), being in second portion 402, do not shift with respect to the baseline. Lastly, FIG. 8(h) is a screenshot taken at time $t_7$, wherein it is seen that δ'(2) was swept back upward before scrolling over to the second portion 402. A new waveform δ'(3) now appears in the first portion 404, while δ'(0) has completely scrolled off the left side of the display. Thus, by viewing FIGS. 8(a) through 8(h), a measure of appreciation for the "whiplike" corrective action in the first portion 404 of the display is attained.

Figure 9A:
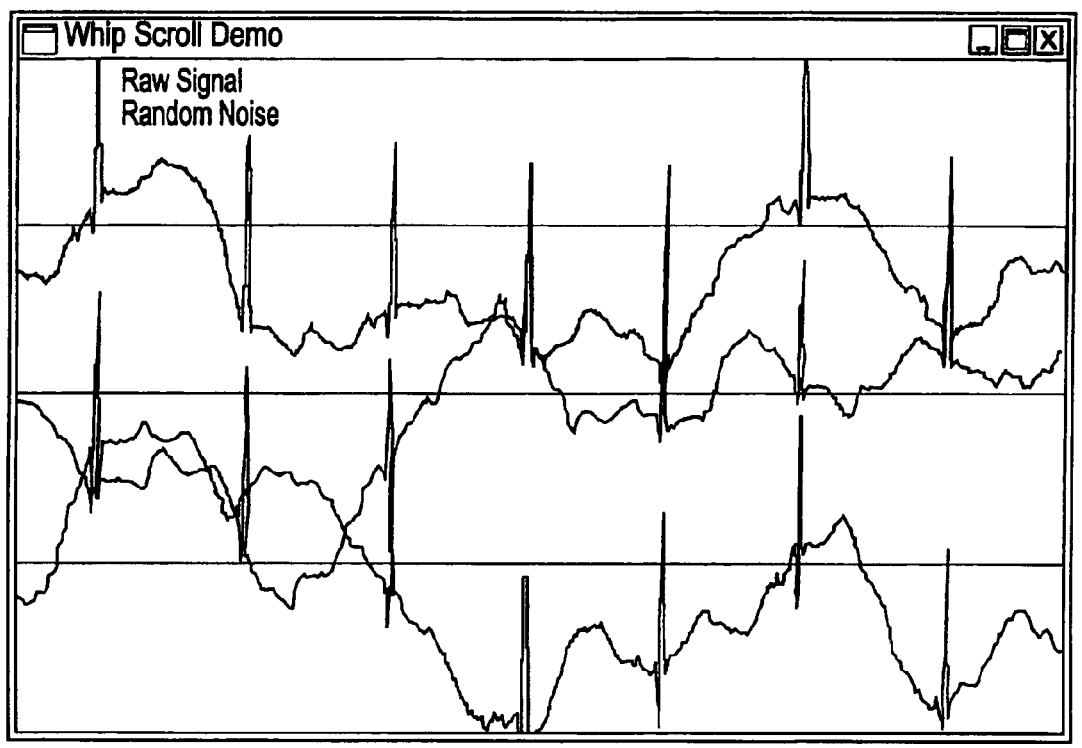
FIGS. 9(a) through 9(e) are waveform displays comparing the results of the inventive data filtering and display technique and the conventional techniques as applied to a repeated example of the same actual ECG data.
Figure 9B:
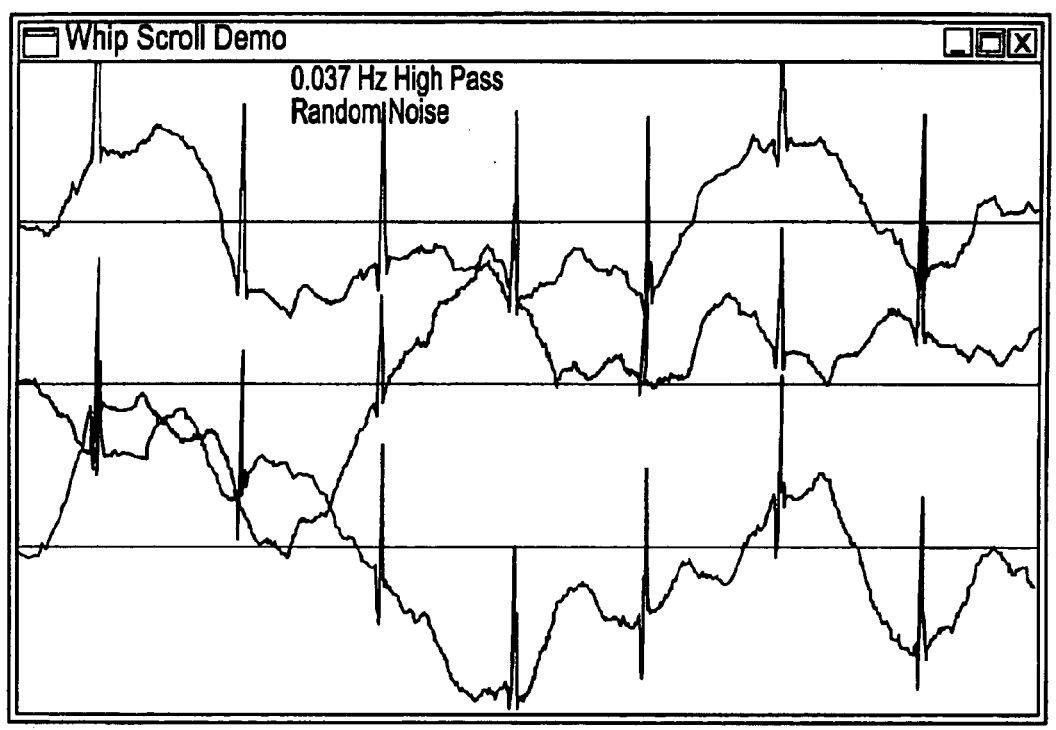
Figure 9C:
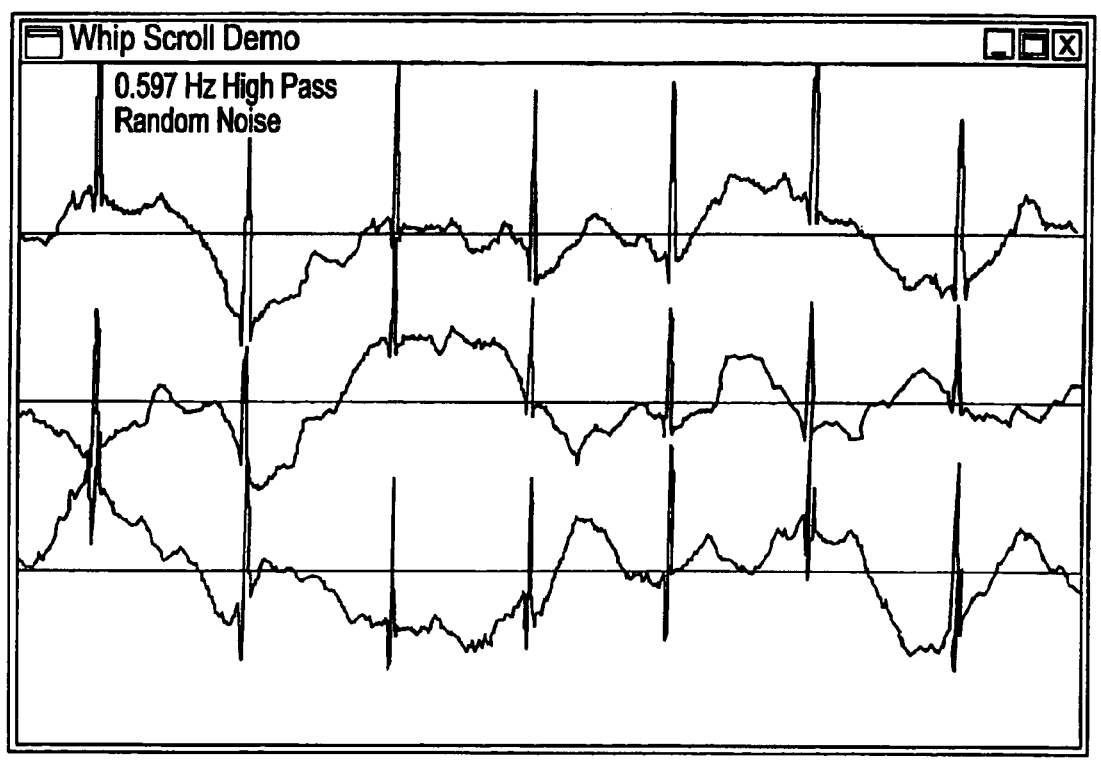
Figure 9D:
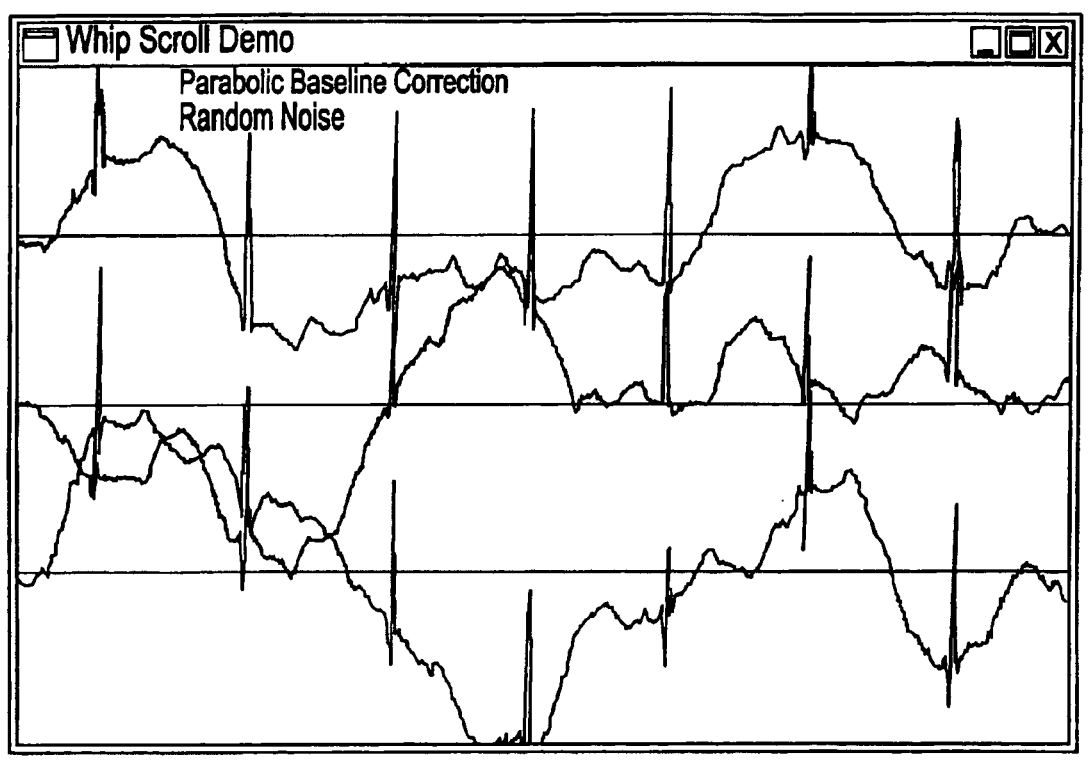
Figure 9E:
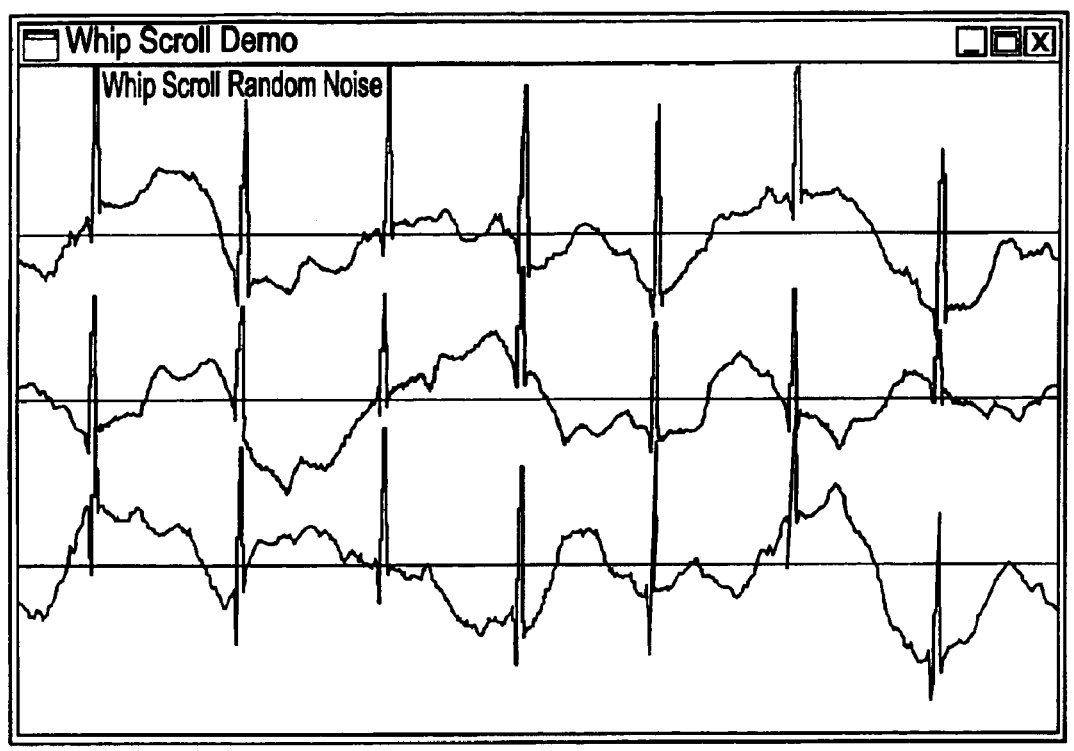

Finally, the results of the present method are compared with the previously discussed conventional filtering techniques, as applied to actual ECG wave forms shown in FIGS. 9(a) through 9(e). In FIG. 9(a), there are three individual ECG raw signal readings, wherein the random noise has actually caused the lower two waveforms to cross over one another. In FIG. 9(b), the same noise has not been effectively remedied by the 0.037 Hz high pass filter, as the two lower waveforms are still crisscrossed. The 0.597 Hz high pass filter does provide the aggressive base line correction by untangling the lower two waveforms in FIG. 9(c), but again the signal distortion can lead to a misinterpretation of the ECG. In FIG. 9(d), the parabolic baseline correction is relatively ineffective like the 0.037 Hz filter. However, FIG. 9(e) shows that the present method is most effective in removing baseline drift without distorting the ECG.

The applicability of the above described method includes all real-time cardiac monitors, invasive electrophysiological (EP) systems, exercise stress test machines, defibrillators, and ECG carts with a real-time rhythm mode and CRT or LCD displays. However, the data filtering and display techniques are not limited to display of ECG data, but may generally apply to any system in which it is desired to display waveform data in real time, such as plethysmograph data, blood pressure data or geologic/seismic data, for example.

In addition the present technique is not limited to just a scrolling wave form display, but may also be used with a "wiper bar" display. In a wiper bar display, a narrow vertical bar typically moves left-to-right across a display screen, wherein the most recent waveform data immediately trails the bar on the left side thereof. When the bar reaches the end of the screen on the right, it wraps back around to the left side of the screen and subsequently erases the older data to the right of the bar. In this type of display, the wiper bar could have (for example) a 1 second trailing window in which the data is continuously level adjusted, partially correcting the baseline. The remaining data on the screen is baseline corrected and not further level adjusted before being finally erased.

As will be appreciated, the disclosed invention can be embodied in the form of computer or controller implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the invention. The present invention may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for displaying waveform data on a display device, the method comprising:

apportioning a display region into a first portion and a second portion immediately adjacent to said first portion;

said first portion being used to display a first segment of the waveform data, said first segment comprising the most recently received data extending back to a determined delay period;

said second portion being used to display a second segment of the waveform data, said second segment comprising the remainder of the waveform data;

wherein the data displayed in said first portion has a continuously varying amplitude level adjustment applied thereto for partial baseline correction thereof, and the data displayed in said second portion has a corrected baseline amplitude adjustment with no further amplitude level adjustment applied thereto.

2. The method of claim 1, wherein said baseline adjustment is applied through a symmetrical finite impulse response filter.

3. The method of claim 2, wherein said symmetrical finite impulse response filter is centered about a given data sample at a time delay of about 0.5 to about 3.0 seconds.

4. The method of claim 1, wherein:

the waveform data is scrolled across said display region such that the waveform data initially appears in said first portion, thereafter scrolling through said first portion while being subjected to said baseline amplitude adjustment, and thereafter appearing in and scrolling through said second portion with no further baseline adjustment being applied thereto.

5. The method of claim 1, wherein:

a wiper bar is scrolled across said display region such that said first portion of said display region adjacently follows said wiper bar along an edge thereof.

6. A method of filtering and displaying sequential waveform data samples, the method comprising:

shifting a sequence of stored uncorrected data samples;

receiving and storing a new uncorrected data sample;

computing a baseline estimate correction using said stored uncorrected data samples and said new uncorrected data sample;

shifting a sequence of stored corrected data samples and thereafter determining a new corrected data sample, wherein said new corrected data sample is determined by applying said baseline estimate correction to a specific one of said stored uncorrected data samples;

creating a sequence of temporary display data samples by applying said baseline correction to each of said stored uncorrected data samples that were stored subsequent to said specific one of said stored uncorrected data samples, as well as to said new uncorrected data sample; and displaying said sequence of corrected data samples, said new corrected data sample, and said sequence of temporary display data samples.

7. The method of claim 6, wherein said baseline estimate correction is implemented by a symmetrical finite impulse response filter.

8. The method of claim 7, wherein said specific one of said stored uncorrected data samples is centrally located within said stored uncorrected data samples.

9. The method of claim 7, wherein said baseline estimate correction is applied at a delay of about 0.5 to about 3.0 seconds with respect to said receiving and storing a new uncorrected data sample.

10. The method of claim 6, wherein said waveform data samples represent electrocardiogram data.

11. An electrocardiogram (ECG) system, comprising:

a set of electrodes for detecting ECG signals from a subject;

signal condition circuitry for conditioning said ECG signals detected by said set of electrodes;

a processor for processing conditioned signals from said signal condition circuitry; and a display for displaying ECG waveform data produced by said processor, said display further comprising:

a display region having a first portion and a second portion immediately adjacent to said first portion;

said first portion being used to display a first segment of said waveform data, said first segment comprising the most recently received data extending back to a determined delay period; and said second portion being used to display a second segment of said waveform data, said second segment comprising the remainder of said waveform data;

wherein said waveform data displayed in said first portion has a continuously varying amplitude level adjustment applied thereto for partial baseline correction thereof, and the data displayed in said second portion has a corrected baseline amplitude adjustment with no further amplitude level adjustment applied thereto.

12. The ECG system of claim 11, wherein said baseline adjustment is applied through a symmetrical finite impulse response filter.

13. The ECG system of claim 12, wherein said symmetrical finite impulse response filter is centered about a given data sample at a time delay of about 0.5 to about 3.0 seconds.

14. The ECG system of claim 11, wherein:

said waveform data is scrolled across said display region such that said waveform data initially appears in said first portion, thereafter scrolling through said first portion while being subjected to said baseline amplitude adjustment, and thereafter appearing in and scrolling through said second portion with no further baseline adjustment being applied thereto.

15. The ECG system of claim 11, wherein:

a wiper bar is scrolled across said display region such that said first portion of said display region adjacently follows said wiper bar along an edge thereof.

16. A storage medium, comprising:

a machine readable computer program code for filtering and displaying sequential waveform data samples; and instructions for causing a computer to implement a method, the method further comprising:

shifting a sequence of stored uncorrected data samples;

receiving and storing a new uncorrected data sample;

computing a baseline estimate correction using said stored uncorrected data samples and said new uncorrected data sample;

shifting a sequence of stored corrected data samples and thereafter determining a new corrected data sample, wherein said new corrected data sample is determined by applying said baseline estimate correction to a specific one of said stored uncorrected data samples;

creating a sequence of temporary display data samples by applying said baseline correction to each of said stored uncorrected data samples that were stored subsequent to said specific one of said stored uncorrected data samples, as well as to said new uncorrected data sample; and displaying said sequence of corrected data samples, said new corrected data sample, and said sequence of temporary display data samples.

17. The storage medium of claim 16, wherein said baseline estimate correction is implemented by a symmetrical finite impulse response filter.

18. The storage medium of claim 17, wherein said specific one of said stored uncorrected data samples is centrally located within said stored uncorrected data samples.

19. The storage medium of claim 17, wherein said baseline estimate correction is applied at a delay of about 0.5 to about 3.0 seconds with respect to said receiving and storing a new uncorrected data sample.

20. The storage medium of claim 16, wherein said waveform data samples represent electrocardiogram data.

21. A computer data signal, comprising:

code configured to cause a processor to implement a method for, the method further comprising:

shifting a sequence of stored uncorrected data samples;

receiving and storing a new uncorrected-data sample;

computing a baseline estimate correction using said stored uncorrected data samples and said new uncorrected data sample;

shifting a sequence of stored corrected data samples and thereafter determining a new corrected data sample, wherein said new corrected data sample is determined by applying said baseline estimate correction to a specific one of said stored uncorrected data samples;

creating a sequence of temporary display data samples by applying said baseline correction to each of said stored uncorrected data samples that were stored subsequent to said specific one of said stored uncorrected data samples, as well as to said new uncorrected data sample; and displaying said sequence of corrected data samples, said new corrected data sample, and said sequence of temporary display data samples.

22. The computer data signal of claim 21, wherein said baseline estimate correction is implemented by a symmetrical finite impulse response filter.

23. The computer data signal of claim 22, wherein said specific one of said stored uncorrected data samples is centrally located within said stored uncorrected data samples.

24. The computer data signal of claim 22, wherein said baseline estimate correction is applied at a delay of about 0.5 to about 3.0 seconds with respect to said receiving and storing a new uncorrected data sample.

25. The computer data signal of claim 21, wherein said waveform data samples represent electrocardiogram data.

* * * * *